(12) United States Patent  (10) Patent No.: US 8,535,429 B2
Grill  (45) Date of Patent: Sep. 17, 2013

(54) CAUSTIC SCRUBBER SYSTEM AND METHOD FOR BIOGAS TREATMENT

(75) Inventor: Jeffrey J. Grill, Long Beach, CA (US)

(73) Assignee: Clean Energy Renewable Fuels, LLC, Newport Beach, CA (US)

( * ) Notice: Subject to any disclaimer, the term of this patent is extended or adjusted under 35 U.S.C. 154(b) by 0 days.

(21) Appl. No.: 13/276,199

(22) Filed: Oct. 18, 2011

(65) Prior Publication Data

US 2013/0092627 A1 Apr. 18, 2013

(51) Int. Cl.
 *B01D 53/14* (2006.01)

(52) U.S. Cl.
 USPC ............... 96/270; 95/230; 95/232; 95/233; 95/235; 96/272; 96/273; 96/322; 210/605; 210/631

(58) Field of Classification Search
 None
 See application file for complete search history.

(56) References Cited

U.S. PATENT DOCUMENTS

| | | | |
|---|---|---|---|
| 3,702,292 A | 11/1972 | Burich | |
| 4,157,247 A * | 6/1979 | Collins et al. | 95/93 |
| 5,352,115 A | 10/1994 | Klobucar | |
| 5,543,122 A | 8/1996 | Hammond et al. | |
| 6,056,934 A | 5/2000 | Carlsen et al. | |
| 6,136,144 A | 10/2000 | Martin et al. | |
| 6,254,779 B1 | 7/2001 | Jeffery et al. | |
| 7,531,159 B2 * | 5/2009 | Lanning et al. | 423/573.1 |
| 7,731,779 B2 | 6/2010 | Palumbo | |
| 2002/0079266 A1 * | 6/2002 | Ainsworth et al. | 210/603 |
| 2005/0132883 A1 * | 6/2005 | Su et al. | 95/235 |
| 2005/0211090 A1 | 9/2005 | McCullough | |
| 2007/0289448 A1 * | 12/2007 | Silva et al. | 95/273 |
| 2008/0210089 A1 * | 9/2008 | Tsangaris et al. | 95/90 |
| 2009/0029062 A1 | 1/2009 | Bar | |
| 2009/0031630 A1 | 2/2009 | Naphad et al. | |
| 2009/0130008 A1 * | 5/2009 | Funk | 423/224 |
| 2009/0206028 A1 * | 8/2009 | Jiang et al. | 210/603 |
| 2009/0239279 A1 * | 9/2009 | Hall et al. | 435/167 |
| 2010/0021979 A1 | 1/2010 | Facey et al. | |
| 2010/0275781 A1 | 11/2010 | Tsangaris et al. | |
| 2011/0033356 A1 | 2/2011 | Mazumdar et al. | |
| 2011/0042307 A1 * | 2/2011 | VanOrnum et al. | 210/603 |

(Continued)

FOREIGN PATENT DOCUMENTS

| | | |
|---|---|---|
| GB | 2207872 | 2/1989 |
| WO | 99/29413 | 6/1999 |

OTHER PUBLICATIONS

Patent Cooperation Treaty, International Search Report, PCT/US2012/060886, Jan. 7, 2013, pp. 1-2.

(Continued)

*Primary Examiner* — Duane Smith
*Assistant Examiner* — Pankti Patel
(74) *Attorney, Agent, or Firm* — Sheppard Mullin Richter & Hampton LLP

(57) ABSTRACT

The present invention provides a method and apparatus for the treat en of process gas from an anaerobic digestion system or a landfill gas system. In one embodiment, the system comprises a caustic scrubber including a vertical column having a top and a bottom and including a counter current flow system, wherein a process gas stream flows up vertically through the column in counter current flow to a caustic liquid solution that flows downward through the column. The caustic liquid solution removes at least one acid from the process gas stream, wherein treated gas that is substantially free of acids bubbles out through an opening at the top of the vertical column.

14 Claims, 2 Drawing Sheets

(56) References Cited

U.S. PATENT DOCUMENTS

| | | |
|---|---|---|
| 2011/0091953 A1 | 4/2011 | Bolin et al. |
| 2011/0244555 A1* | 10/2011 | Gunther ........................ 435/266 |
| 2012/0049114 A1* | 3/2012 | Seeker et al. .................. 252/184 |
| 2012/0076716 A1* | 3/2012 | Suchak et al. ............. 423/437.1 |

OTHER PUBLICATIONS

Patent Cooperation Treaty, International Search Report, PCT/US2012/060882, Dec. 17, 2012, pp. 1-2.

* cited by examiner

CAUSTIC SCRUBBER SYSTEM AND METHOD FOR BIOGAS TREATMENT

FIELD OF THE INVENTION

The invention broadly relates to biogas applications and, more particularly, to a caustic scrubber system and method for biogas treatment.

BACKGROUND OF THE INVENTION

Biogas refers to a gaseous fuel produced by the biological breakdown of organic matter in the absence of oxygen. It is produced by the anaerobic digestion or fermentation of biodegradable materials such as biomass, manure, sewage, municipal waste, green waste, plant material and crops. Biogas primarily comprises ethane and carbon dioxide, and may contain small amounts of hydrogen sulphide, moisture and siloxanes.

The gases methane, hydrogen and carbon monoxide can be combusted or oxidized with oxygen. This energy release allows biogas to be used as a fuel. Biogas can be used as a fuel for any heating purpose. It can also be produced by anaerobic digesters where it is typically used in a gas engine to convert the chemical energy of the gas into electricity and heat. Anaerobic digestion is a series of processes in which microorganisms break down biodegradable material in the absence of oxygen, also used for industrial or domestic purposes to manage waste and/or to release energy.

The digestion process begins with bacterial hydrolysis of the input materials in order to break down insoluble organic polymers such as carbohydrates and make them available for other bacteria. Acidogenic bacteria then convert the sugars and a amino acids into carbon dioxide, hydrogen, ammonia, and organic acids. These bacteria then convert these resulting organic acids into acetic acid, along with additional ammonia, hydrogen, and carbon dioxide. Finally, methanogens convert these products to methane and carbon dioxide.

Anaerobic digesters can use a multitude of feed stocks for the production of methane rich bio-gas including but not limited to purpose-grown energy crops such as maize. Landfills also produce methane rich bio-gas through the anaerobic digestion process. As part of an integrated waste management system, this bio-gas may be collected and processed for beneficial use while simultaneously reducing greenhouse gas emissions into the atmosphere.

Anaerobic digestion is widely used as a source of renewable energy. The process produces a biogas that can be used directly as cooking fuel, in combined heat and power gas engines or upgraded to natural gas quality biomethane. The utilization of biogas as a fuel helps to replace fossil fuels. The nutrient-rich digestate and/or Leachate that is also produced can be used as fertilizer.

The technical expertise required to maintain industrial scale anaerobic digesters coupled with high capital costs and low process efficiencies have limited the level of its industrial application as a waste treatment technology. As a result, it is imperative that anaerobic digesters and landfill gas treatment plants operate at the highest possible efficiency.

In biogas applications such as landfills and digesters, $H_2S$ and other impurities including halides and halogenated compounds are frequently present in low percent to ppm/ppb quantities. These compounds may dissociate at high temperatures and in the presence of water to form caustic acids including, but not limited to $H_2S$, $HF$, $H_2SO_4$, $H_3PO_4$ and $HNO_3$.

Typical metallurgy such as carbon and stainless steels are susceptible to corrosion and failure when placed into contact with these acids. Downstream equipment that changes the dew point and allows condensation to occur may concentrate these acids in pooling areas such as moisture separators, chillers, and gas coolers.

Gas processing techniques and other unit operations may produce acids form gas constituents. However, these systems merely employ acid neutralization after the acids have formed and concentrated in the pooling areas. As such, these conventional systems simply act as a band aid to condensation. Caustic scrubbers have been used in the past for several applications. For example, they may be used for $CO_2$ removal, $H_2S$ removal and also for the removal of several other reactive contaminants in both liquid and gaseous phase.

SUMMARY OF THE INVENTION

The present invention provides a caustic scrubber system and method for biogas treatment. The caustic scrubber may be used to neutralize acids such as $H_2S$, $HF$, $H_2SO_4$, $H_3PO_4$ and $HNO_3$ in either the liquid or gaseous phase to protect downstream metallurgy and equipment.

One embodiment of the invention is directed toward an apparatus for the treatment of process gas from an anaerobic digestion system or a landfill gas system, the apparatus comprising a caustic scrubber including a vertical column having a top and a bottom and including a counter current flow system, wherein a process gas stream flows up vertically through the column in counter current flow to a caustic liquid solution that flows downward through the column. The caustic liquid solution removes at least one acid from the process gas stream, wherein treated gas that is substantially free of acids bubbles out through an opening at the top of the vertical column.

In the above-described apparatus, the at least one acid can be selected from the group consisting of $H_2S$, $HF$, $H_2SO_4$, $H_3PO_4$ and $HNO_3$. In addition, the liquid solution may comprise a basic solution for neutralizing the at least one acid. In one embodiment, the caustic liquid solution comprises an NaOH solution. The caustic liquid solution may be gravity trickled or sprayed within the vertical column. The spent caustic liquid solution containing the at least one acid may flow through an opening in the bottom of the column and into a neutralization tank.

According to some embodiments, the treated gas flows back into the anaerobic digestion system. In one implementation, the caustic scrubber is located within the aerobic digestion system between an anaerobic digester and a biogas handling system in order to protect the biogas handling system and other downstream equipment from corrosion. The caustic scrubber allows for the total removal of $H_2S$, $HF$, $H_2SO_4$, $H_3PO_4$ and $HNO_3$ from the process gas stream so that acid concentration does not occur in any downstream areas regardless of changing dew point and condensation.

Another embodiment of the invention is directed toward an apparatus for the treatment of process gas from a landfill gas system, comprising a caustic scrubber including a vertical column having atop and a bottom and including a counter current flow system, wherein a process gas stream flows up vertically through the column in counter current flow to a caustic liquid solution that flows downward through the column; wherein the caustic liquid solution removes at least one acid from the process gas stream; and wherein treated gas that is substantially free of acids bubbles out through an opening at the top of the vertical column.

Yet another embodiment of the invention comprises a method of using a caustic scrubber for the treatment of process gas from an anaerobic digestion system. In particular, the method may entail: (i) receiving a process gas stream from the anaerobic digestion system; (ii) flowing the process gas stream up vertically through a vertical column; (iii) flowing a caustic liquid solution downward through the vertical column such that the caustic liquid solution removes at least one acid from the process gas stream; (iv) bubbling out treated gas that is substantially free of acids through an opening at the top of the vertical column; and (v) flowing the treated gas into an anaerobic digestion cleanup system.

A further embodiment of the invention comprises a method of using a caustic scrubber for the treatment of process gas from a landfill gas system. Specifically, the method may entail: (i) receiving a process gas stream from the landfill gas system; (ii) flowing the process gas stream up vertically through a vertical column; (iii) flowing a caustic liquid solution downward through the vertical column such that the caustic liquid solution removes at least one acid from the process gas stream; (iv) bubbling out treated gas that is substantially free of acids an opening at the top of the vertical column; and (v) flowing the treated gas into a landfill gas cleanup system.

DETAILED DESCRIPTION

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

Biogas is a renewable energy composed primarily of methane resulting from the natural decomposition of organic waste by anaerobic bacteria. Similar to natural gas, methane captured by a biogas system can be used to provide heat, electrical power or transportation biofuel. Biogas extraction can be used to: (i) produce green and renewable energy; (ii) reduce pollution and greenhouse gases; (iii) reduce waste odors and pathogens; and transform waste into valuable bio-fertilizer.

Fermentation, or anaerobic digestion, is the most common process that breaks down the organic waste. The organic waste may then be oxidized, thereby creating energy. Various types of organic materials include, but are not limited to: (i) biomass, (ii) landfill waste, (iii) sewage, (iv) manure, and (v) plant material. The most common gases produced are methane and carbon dioxide. Other gases that can be formed include hydrogen, nitrogen, and carbon monoxide. Methane, hydrogen, and carbon monoxide can be combusted to create heat and electricity. When biogas is created from existing waste streams, it reduces odors and methane emissions and creates two renewable resources. Methane is a potent greenhouse gas that contributes to global climate change. It is expected that a landfill gas energy project will capture about 60% to 90% of the methane emitted from the landfill, depending on system design and effectiveness.

There are two primary methods of recovering biogas for use as energy, namely: (i) by creating an anaerobic digestion system to process waste, most commonly manure or other wet biomass, and (ii) by recovering natural biogas production formed in existing landfills. Once recovered, biogas can be converted to energy using a number of methods.

Figure 1:
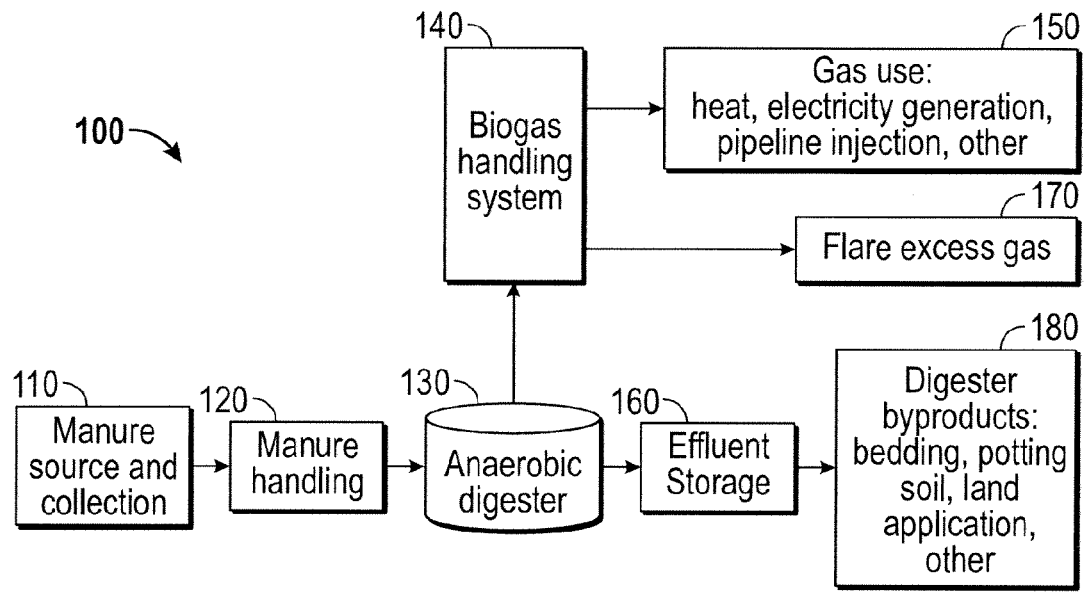
FIG. 1 is a flow diagram illustrating the stages of an exemplary anaerobic digestion system.

FIG. 1 is a flow diagram illustrating the stages of an exemplary anaerobic digestion system 100. Specifically, the an anaerobic digestion system 100 comprises a manure collection system 110, a manure handling system 120, an anaerobic digester 130, a biogas handling system 140, gas use devices 150, an effluent storage 160. In addition, at least one flare 170 may be used to burn excess gas. Digester products 180 may be used for bedding, potting soil, land applications, etc. More particularly, manure collection system 110 is used to gather manure and transport it to the anaerobic digester 130. In some cases, existing liquid/slurry manure management systems can be adapted to deliver manure to the anaerobic digester 130. The anaerobic digester 130 may be designed to stabilize manure and optimize the production of methane. A storage facility for digester effluent, or waste matter, is also required.

With further reference to FIG. 1, the anaerobic digester 130 outputs biogas into the biogas handling system 140. The biogas may contain approximately 60% methane and 40% carbon dioxide. It is collected, treated, and piped to a gas use device 150. By way of example, the biogas can then be upgraded to natural gas pipeline quality. It may also be used to generate electricity, as a boiler fuel for space or water heating, or for a variety of other uses. At least one flare 170 is also installed to destroy extra gas and as a back-up mechanism for the primary gas use device 160.

The anaerobic digester 130 may be made out of concrete, steel, brick, or plastic. Additionally, the digester 130 includes a tank for pre-mixing the waste and a digester vessel. In some embodiments, the anaerobic digester 130 may comprise a batch digesters or a continuous digester. A batch digester is loaded with organic materials, which are allowed to digest therein. The retention time depends on temperature and other factors. Once the digestion is complete, the effluent is removed and the process is repeated.

In further embodiments, the anaerobic digester 130 may comprise a continuous digester, wherein organic material is constantly or regularly fed into the digester, and wherein the material moves through the digester either mechanically or by the force of the new feed. Unlike batch-type digesters, continuous digesters produce biogas without the interruption of loading material and unloading effluent. Various types of continuous digesters include vertical tank systems, horizontal tank or plug-flow systems, and multiple tank systems.

Anaerobic digestion also occurs naturally underground in landfills, wherein the waste is covered and compressed by the weight of the material that is deposited above. This material prevents oxygen exposure, thereby allowing chemical reactions and microbes to act upon the waste. This encourages an uncontrolled process of biomass decay. The rate of production is affected by waste composition and landfill geometry. Landfill gas may comprise about 40% to 60% methane, and about 40% to 60% carbon dioxide.

Figure 2:
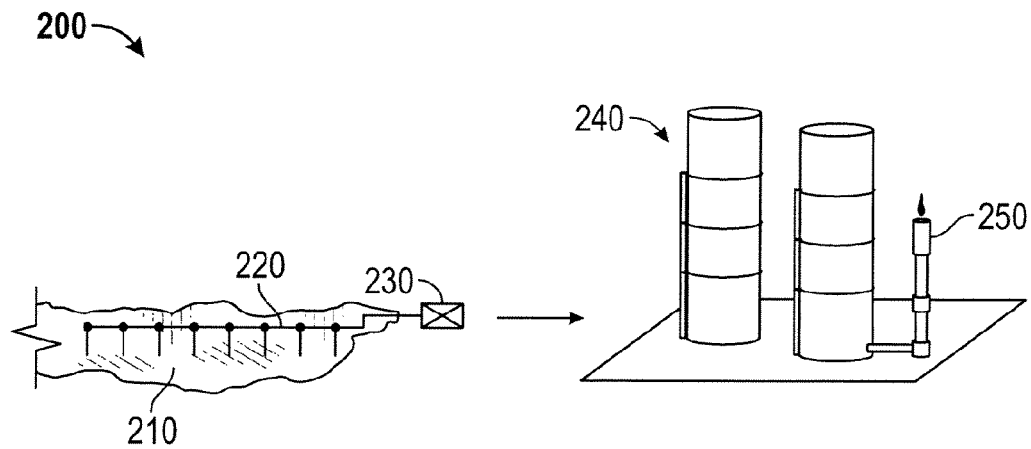
FIG. 2 is a diagram illustrating the stages of an exemplary landfill gas system.

FIG. 2 is a diagram illustrating an exemplary landfill gas system 200 including landfill 210, landfill gas wells 220 for active gas collection, landfill gas wellhead 230, landfill gas processing and treatment plant 240, and at least one landfill gas flare 250. Landfill gas is extracted from landfill 210 using a series of wells 220 and a blower/flare system. The landfill gas system 200 directs the collected gas to landfill gas processing and treatment plant 240, where it is processed and treated.

Figure 3:
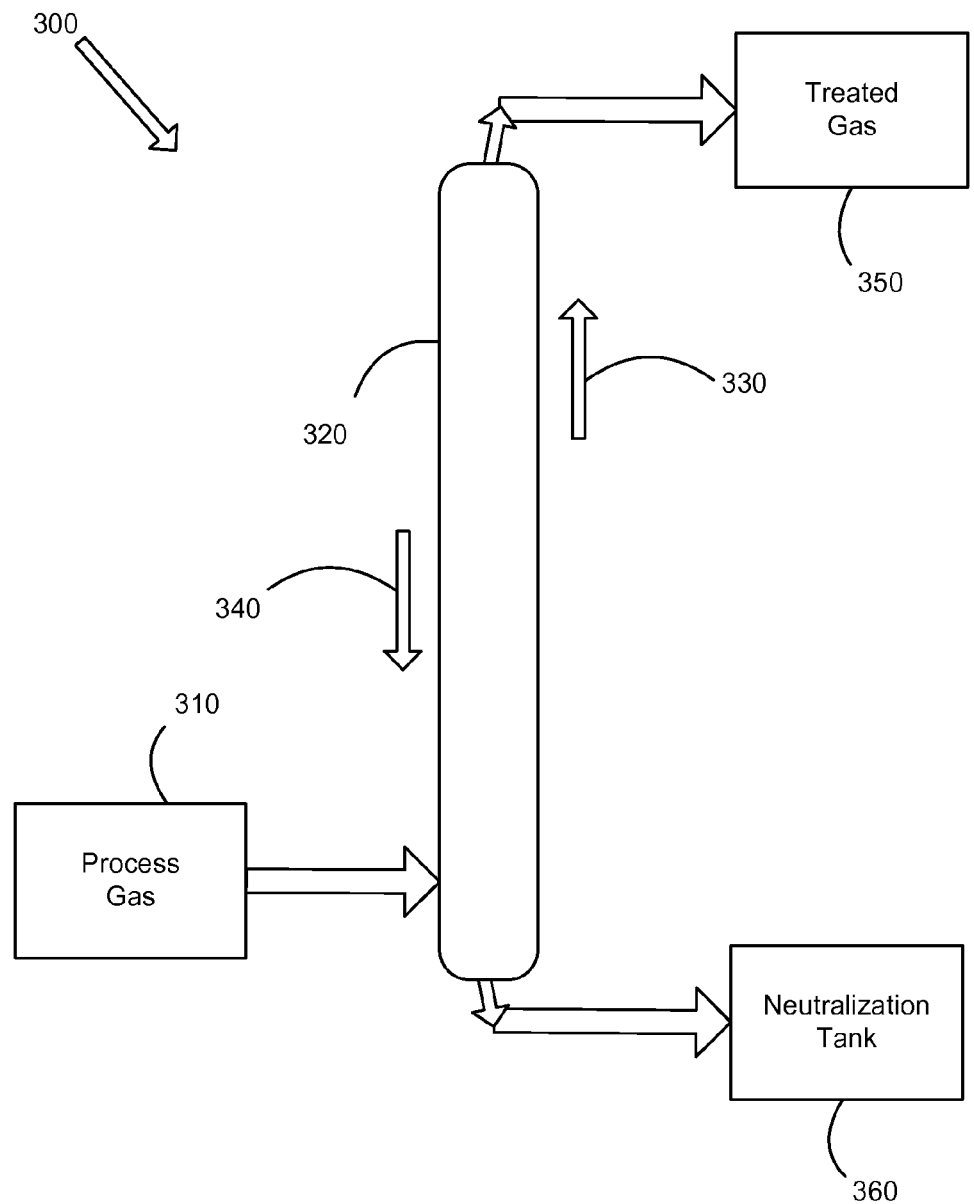
FIG. 3 is a illustrating the use of a caustic scrubber system in accordance with an embodiment of the invention.

FIG. 3 is a diagram illustrating the use of a caustic scrubber system 300 in accordance with an embodiment of the invention. In particular, process gas 310 (e.g., from an anaerobic digestion system 100 or a landfill gas system 200) is fed into the caustic scrubber 320. Process gas 310 contains at least one acid selected from the group consisting of $H_2S$, HF, $H_2SO_4$, $H_3PO_4$ and $HNO_3$. Such acids may be present in liquid and/or gaseous phases. According to various embodiments, the caustic scrubber 320 comprises a vertical column and includes a counter current flow system, wherein the gas stream travels up vertically through the column (as indicated by arrow 330) in counter current flow to a gravity trickling or sprayed caustic liquid solution that flows downward within the column (as indicated by arrow 340). The caustic liquid solution comprises a basic solution that is employed to neutralize various acids that are likely to be present in the process gas 310 such as $H_2S$, HF, $H_2SO_4$, $H_3PO_4$ and $HNO_3$. By way of example, the caustic liquid solution may comprise an NaOH solution. This process results in treated gas 350 that is substantially free of acids bubbling out through an opening at the top of the caustic scrubber 320. The spent caustic liquid solution containing acids flows through an opening in the bottom of the column and into a neutralization tank 360.

With further reference to FIG. 3, the treated gas 350 that is substantially free of acids flows back into the anaerobic digestion system 100 (FIG. 1) or the landfill gas system 200 (FIG. 2). In order to protect downstream metallurgy and equipment, acoustic scrubber 320 may be located, for example, between the anaerobic digester 130 and the biogas handling system 140 (FIG. 1) in order to protect the biogas handling system 140 and other downstream equipment from corrosion and other deleterious effects. Additionally, a caustic scrubber 320 may be located between the landfill gas wells 220 and the landfill gas processing and treatment plant 240 (FIG. 2) in order to protect the landfill gas processing and treatment plant 240 and other downstream equipment from corrosion. According to some embodiments of the invention, the caustic scrubber allows for the total removal of acids such as $H_2S$, HF, $H_2SO_4$, $H_3PO_4$ and $HNO_3$ from the gas stream so that acid concentration cannot occur in any downstream areas regardless of changing dew point and condensation.

Another embodiment of the invention comprises a method of using a caustic scrubber for the treatment of process gas from an anaerobic digestion system. In particular, the method may entail: (i) receiving a process gas stream from the anaerobic digestion system; (ii) flowing the process gas stream up vertically through a vertical column; (iii) flowing a caustic liquid solution downward through the vertical column such that the caustic liquid solution removes at least one acid from the process gas stream; (iv) bubbling out treated gas that is substantially free of acids an opening at the top of the vertical column; and (v) flowing the treated gas into an anaerobic digestion cleanup system.

A further embodiment of the invention comprises a method of using a caustic scrubber for the treatment of process gas from a landfill gas system. Specifically, the method may entail: (i) receiving a process gas stream from the landfill gas system; (ii) flowing the process gas stream up vertically through a vertical column; (iii) flowing a caustic liquid solution downward through the vertical column such that the caustic liquid solution removes at least one acid from the process gas stream; (iv) bubbling out treated gas that is substantially free of acids an opening at the top of the vertical column; and (v) flowing the treated gas into a landfill gas cleanup system.

One skilled in the art will appreciate that the present invention can be practiced by other than the various embodiments and preferred embodiments, which are presented in this description for purposes of illustration and not of limitation, and the present invention is limited only by the claims that follow. It is noted that equivalents for the particular embodiments discussed in this description may practice the invention as well.

While various embodiments of the present invention have been described above, it should be understood that they have been presented by way of example only, and not of limitation. Likewise, the various diagrams may depict an example architectural or other configuration for the invention, which is done to aid in understanding the features and functionality that may be included in the invention. The invention is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the present invention. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof: the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/ or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a co on package. Indeed, any or all of the various components of a module, whether control logic or other components, may be combined in a single package or separately maintained and may further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

The invention claimed is:

1. Apparatus for the treatment of process gas, comprising:
    an anaerobic digestion system comprising a manure collection system for gathering manure and transporting it to an anaerobic digester, an anaerobic digester, and a biogas handling system for upgrading biogas from the digester to a process gas that is natural gas pipeline quality;
    a caustic scrubber comprising a vertical column having a top and a bottom and including a counter current flow system, wherein the process gas stream flows up vertically through the column in counter current flow to a caustic liquid solution that flows downward through the column;
    wherein the caustic liquid solution comprises an NaOH solution;
    wherein the caustic liquid solution removes at least one acid from the process gas stream; and
    wherein treated gas that is substantially free of acids bubbles out through an opening at the top of the vertical column.

2. The apparatus of claim 1, wherein the at least one acid comprises an acid selected from the group consisting of $H_2S$, HF, $H_2SO_4$, $H_3PO_4$ and $HNO_3$.

3. The apparatus of claim 1, wherein the caustic liquid solution is gravity trickled or sprayed within the vertical column.

4. The apparatus of claim 1, wherein spent caustic liquid solution containing the at least one acid flows through an opening in the bottom of the column and into a neutralization tank.

5. The apparatus of claim 1, wherein the treated gas flows back into the anaerobic digestion system.

6. The apparatus of claim 1, wherein the caustic scrubber is located within the anaerobic digestion system between the anaerobic digester and the biogas handling system in order to protect the biogas handling system and other downstream equipment from corrosion.

7. The apparatus of claim 1, wherein the caustic scrubber allows for the total removal of $H_2S$, HF, $H_2SO_4$, $H_3PO_4$ and $HNO_3$ from the process gas stream so that acid concentration does not occur in any downstream areas regardless of changing dew point and condensation.

8. Apparatus for the treatment of process gas, comprising:
    a landfill gas system comprising landfill gas wells for active gas collection from a landfill, and a landfill gas processing and treatment plant;
    a caustic scrubber comprising a vertical column having a top and a bottom and including a counter current flow system, wherein the process gas stream flows up vertically through the column in counter current flow to a caustic liquid solution that flows downward through the column;
    wherein the caustic liquid solution comprises an NaOH solution;
    wherein the caustic liquid solution removes at least one acid from the process gas stream; and
    wherein treated gas that is substantially free of acids bubbles out through an opening at the top of the vertical column.

9. The apparatus of claim 8, wherein the at least one acid comprises an acid selected from the group consisting of $H_2S$, HF, $H_2SO_4$, $H_3PO_4$ and $HNO_3$.

10. The apparatus of claim 8, wherein the caustic liquid solution is gravity trickled or sprayed within the vertical column.

11. The apparatus of claim 8, wherein spent caustic liquid solution containing the at least one acid flows through an opening in the bottom of the column and into a neutralization tank.

12. The apparatus of claim 8, wherein the treated gas flows back into the landfill gas system.

13. The apparatus of claim 8, wherein the caustic scrubber is located within the landfill gas system between the landfill gas wells and the landfill gas processing and treatment plant in order to protect the landfill gas processing and treatment plant and other downstream equipment from corrosion.

14. The apparatus of claim 8, wherein the caustic scrubber allows for the total removal of $H_2S$, HF, $H_2SO_4$, $H_3PO_4$ and $HNO_3$ from the process gas stream so that acid concentration cannot occur in any downstream areas regardless of changing dew point and condensation.

* * * * *

UNITED STATES PATENT AND TRADEMARK OFFICE
CERTIFICATE OF CORRECTION

PATENT NO. : 8,535,429 B2
APPLICATION NO. : 13/276199
DATED : September 17, 2013
INVENTOR(S) : Jeffrey J. Grill Page 1 of 1

It is certified that error appears in the above-identified patent and that said Letters Patent is hereby corrected as shown below:

In the Specification:

Column 1, line 17: "ethane" should be -- methane --.

Column 1, line 34: "and a amino" should be -- and amino --.

Column 2, line 46: "aerobic" should be -- anaerobic --.

Column 2, line 57: "atop" should be -- a top --.

Column 5, line 32: "acoustic" should be -- a caustic --.

Column 6, line 52: "thereof:" should be -- thereof; --.

Column 7, line 16: "co on" should be -- common --.

Signed and Sealed this
Fifth Day of November, 2013

Teresa Stanek Rea
*Deputy Director of the United States Patent and Trademark Office*